US006184377B1

(12) United States Patent
Gao

(10) Patent No.: US 6,184,377 B1
(45) Date of Patent: Feb. 6, 2001

(54) COMPOSITIONS CONTAINING N-AMINO- AND N-HYDROXY-QUINAZOLINONES AND METHODS FOR PREPARING LIBRARIES THEREOF

(75) Inventor: Yun Gao, Southborough, MA (US)

(73) Assignee: Sepracor Inc., Marlborough, MA (US)

( * ) Notice: Under 35 U.S.C. 154(b), the term of this patent shall be extended for 0 days.

(21) Appl. No.: 08/990,855

(22) Filed: Dec. 15, 1997

(51) Int. Cl.$^7$ .................................................. C07D 239/92
(52) U.S. Cl. ..................... 544/234; 544/233; 544/247; 544/250; 544/251; 544/284; 544/285; 544/287; 544/289
(58) Field of Search ..................... 544/247, 250, 544/251, 284, 285, 289, 233, 234, 287

(56) References Cited

U.S. PATENT DOCUMENTS

| | | | |
|---|---|---|---|
| 3,322,766 | 5/1967 | Schipper ............................ | 260/256.4 |
| 3,528,982 | 9/1970 | Cusie et al. ...................... | 260/256.4 |
| 3,635,976 | 1/1972 | Shetty .............................. | 260/256.4 |
| 3,812,257 | 5/1974 | Yamamoto et al. ................ | 424/251 |
| 3,865,827 | 2/1975 | Yamamoto et al. ............ | 260/251 A |
| 4,096,144 | 6/1978 | Yamamoto et al. ................ | 544/284 |
| 4,099,002 | 7/1978 | Inaba et al. ......................... | 544/119 |
| 4,335,127 | 6/1982 | Vandenberk et al. ............... | 424/251 |
| 5,143,854 | 9/1992 | Pirrung et al. ..................... | 436/518 |
| 5,164,371 | 11/1992 | Edwards et al. ................... | 514/18 |
| 5,169,952 | 12/1992 | Askin et al. ....................... | 544/137 |
| 5,354,755 | * 10/1994 | Takasugi et al. .................. | 514/259 |
| 5,783,698 | * 7/1998 | Smith ................................. | 544/285 |

OTHER PUBLICATIONS

R. M. Christie, and S. Moss, "Cyclisation of Schiff Bases Containing Amide or Hydroxamic Acid Groups to 1,2–Dihydroquinazolin–4–ones; Thermal Decomposition Reactions of the 1,2–Dihydroquinazolin–4–ones" *J. Chem. Soc. Perkin. Trans. I* , 2779–2783 (1985).

M. Ghelardoni and V. Pestellini, "Nuovi Derivati Policiclici a Nuclei Condensati Contenenti Il Sistema Del 4–Chinazolone," *Annali di Chimica*, 64:445–453 (1974).

E.M. Gordon et al., "Applications of Combinatorial Technologies to Drug Discovery. 2. Combinatorial organic Synthesis, Library Screening Strategies, and Future Directions", *J. Medicinal Chem.*, 37(10):1385–1401 (1994).

H. Kohl and E. Wolf, "Cyclisierungsreaktionen von o–Acylamino–benzhydroxamsaure–O–alkylestern", *Liebigs Ann. Chem.* 766:106–115 (1972).

C.B. Schapira and S. Lamden, "Cyclic Hydrxamic Acids Derived from Quinazolin", *J. Heterocyclic Chem.*, 9:569–576 (1972).

K. Tanaka et al., "Syntheses of Cyclic Hydroxamic Acid Derivatives, and Their Chelating Abilities and Biological Activites," *Chem. Pharm. Bull.*, 36:2323–2330 (1988).

* cited by examiner

*Primary Examiner*—Richard L. Raymond
(74) *Attorney, Agent, or Firm*—Matthew P. Vincent; Dana M. Gordon; Foley, Hoag & Eliot LLP

(57) ABSTRACT

The present invention is directed to certain N-amino- and N-hydroxy-quinazolinone compounds and synthetic methods for synthesis thereof, which compounds may find use in combinatorial libraries. More specifically, the invention is directed to the synthesis of 3-hydroxy- and 3-amino-4(1H)-quinazolinones via the reaction of an appropriate 2-aminobenzamide compound with a carboxylic acid or acyl halide at ambient temperature performed on a solid support or in solution.

14 Claims, 5 Drawing Sheets

Figure 1:
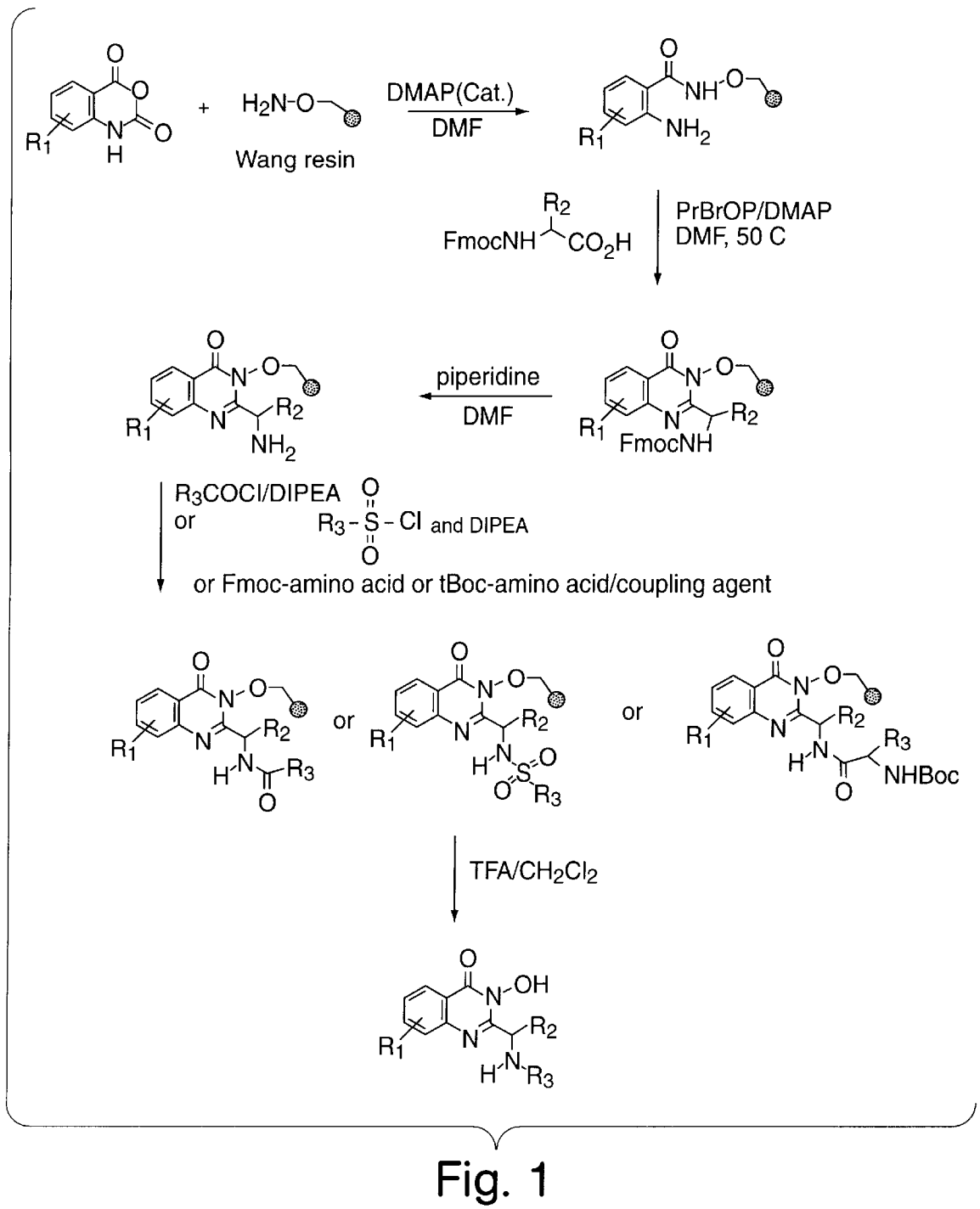

See: von Hans Kohl and E. Wolf, Liebigs *Ann. Chem.* 1972, 766, 106-115

COMPOSITIONS CONTAINING N-AMINO- AND N-HYDROXY-QUINAZOLINONES AND METHODS FOR PREPARING LIBRARIES THEREOF

1. FIELD OF THE INVENTION

The present invention relates to N-hydroxy- and N-amino-quinazolinones and methods for preparing such compounds.

2. BACKGROUND OF THE INVENTION

There is a great interest in synthetic methods directed toward the creation of large collections of small organic compounds, or libraries, which could be screened for pharmacological, biological or other activity. Often referred to as combinatorial chemistry, the synthetic methods applied to create vast combinatorial libraries are performed in solution or in the solid phase, i.e., on a solid support. Further, solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Typically, combinatorial methods involve the addition of various structural components sequentially, either in a controlled or random manner to a core chemical structure in order to produce all or a substantial portion of the possible combinations that can result from the different possible reactions at each stage. The efficient use of this technique can create thousands of compounds for pharmacological screening in a rapid fashion.

Methods for screening libraries of compounds for binding properties to a receptor include methods wherein each member of the library is tagged with a unique identifier to facilitate identification of compounds having binding properties, or where the library comprises a plurality of compounds synthesized at particular locations on the surface of a solid substrate. The receptor may be appropriately labelled with a radioactive or fluorescent label that enables one to ascertain whether binding to the receptor of interest has occurred. Correlation of the labelled receptor bound to the substrate, which has its location on the substrate, identifies the binding ligand as disclosed in U.S. Pat. No. 5,143,854.

In contrast to the standard combinatorial chemistry approach which results in libraries with maximum diversity, there is a trend toward the design of more targeted libraries, particularly of small compounds, which minimize redundancy and improve screening efficiency.

One particular class of compounds that would be useful for inclusion in targeted libraries is quinazolinone compounds such as N-hydroxy-quinazolinones and derivatives thereof. Quinazolinone compounds possess a diverse array of beneficial pharmaceutical and chemical properties. For example, certain quinazolinones are known to possess antipyretic, hypotensive, antibacterial, antifungal or central nervous system (CNS) activity, as well as the ability to inhibit enzymes of biological importance, such as metalloenzymes.

C. Schapira and S. Lamdan (*J. Heterocyclic Chem.*, 9:569–576 (1972)) disclose the action of various simple acylating agents on 2-aminobenzohydroxamic acid, which afforded 3-hydroxy-4(3H)-quinazolinones (hydroxamic acids), as well as several ethers and esters derived therefrom.

H. Kohl and E. Wolf (*Liebigs Ann. Chem.*, 766:106–115 (1972)) disclose that O-alkyl N-acylaminobenzhydroxamates are readily cyclized to 2-substituted-3-alkoxyquinazolinones.

M. Ghelardoni and V. Pestellini (*Annali di Chimica*, 64:445–453 (1974)) disclose the synthesis of fused-ring systems containing the 4-quinazolone nucleus. These compounds are obtained by condensation of o-aminobenzoylhydrazine or o-aminobenzohydroxamic acid with compounds containing both carbonyl and carboxyl groups, such as phthalaldehydic acid or levulinic acid, or with cyclic anhydrides, such as phthalic anhydride or succinic anhydride.

K. Tanaka et al. (*Chem. Pharm. Bull.*, 36(7):2323–2330 (1988)) disclose the synthesis of 3-Hydroxy-4-oxo-3,4 dihydroquinazolinones, which exhibited metal chelating abilities, analgesic activities, and inhibition of the growth of microorganisms. The 3-hydroxy-4-oxo-3,4-dihydroquinazolinones were prepared, for example, by reacting a 2-aminobenzohydroxamic acid with acetic anhydride or formic acid.

Although, a variety of syntheses of quinazolinones using solution-phase techniques have been reported, there is a need for a general method of synthesis of such compounds, especially in the solid phase. In other words, there is a need for a solid-phase synthesis that allows one to synthesize a multiplicity of quinazolinones on a variety of solid supports, as well as a need for preparing and screening a library of quinazolinones for pharmacological or biological activities.

Accordingly, there is a need in the art for an efficient method for obtaining a library of N-hydroxy- and N-amino quinazolinones, particularly 3-hydroxy-quinazolinones and 3-amino-quinazolinones, wherein the starting materials are amenable to large scale synthesis.

Citation or identification of any reference in this section of this application shall not be construed as an admission that such reference is available as prior art to the application.

3. SUMMARY OF THE INVENTION

The present invention is directed to synthesis of N-amino and N-hydroxy-quinazolinone compounds on solid supports. The use of solid support in the present invention both allows for protection of the N-moiety and facilitates purification and/or isolation. The synthesis of the instant invention is particularly useful since mild conditions are involved.

In general terms, the invention involves the coupling of a substituted or unsubstituted isatoic anhydride to a solid support, preferably a solid support containing a hydrazino or hydroxylamine moiety that is available for reaction. This coupling reaction forms a 2-aminobenzamide which is bound to the solid support via the amide-nitrogen, thereby both protecting and anchoring the 2-aminobenzamide. The bound 2-aminobenzamide is subsequently reacted with a compound of the formula

or

wherein X is OH, Cl, F, Br or a carboxylic acid activating group; Y is $NR^3R^4$ where $NR^3R^4$ is an N-protected-amino acid, or Cl, Br, or F and $R^2$ is a substituted or unsubstituted alkyl, aryl, alkylaryl group and W is a heterocyclic group to form a cyclized compound, i.e., a quinazolinone. It should be recognized that a variety of quinazolinone can be prepared depending upon the compound chosen for coupling. Further, the resulting solid-phase bound product can either be further modified or simply cleaved, or both. Thus, a vast number of quinazolinone compounds can be prepared and screened for potential biological activity. In certain embodiments, the resin-bound 2-aminobenzamide is reacted with a carboxylic acid or activated form thereof which is represented by the formula:

$$R^2—CHY—CO—X$$

or $$W—CO—X$$

wherein X is OH, Cl, F, Br or a carboxylic acid activating group; Y is $NR^3R^4$, Cl, Br, F or I; $R^2$ is a substituted or unsubstituted alkyl, aryl, heteroarylalkyl or aralkyl group; $R^3$ and $R^4$ are suitable NH protecting groups; and W is a heterocyclic group.

The present invention is directed, in one of its aspects, to general synthetic methods for incorporating a N-amino or N-hydroxy-4(1H)-quinazolinone of the formula (I) onto a solid support.

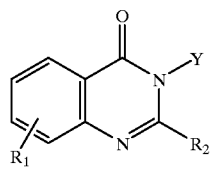

(I)

wherein $R^1$ is an independently selected mono-, di-, tri-, or quad-substitutent on the phenyl ring, and where $R^1$ is independently hydrogen, halogen, $C_1$–$C_6$ alkyl, $C_2$–$C_6$ alkenyl, $C_2$–$C_6$ alkynyl optionally substituted with halogen, hydroxy, $C_1$–$C_6$ alkoxy and aryl, or hydroxy, $C_1$–$C_6$ alkoxy, $NO_2$, $SO_2Ph$, phenyl $SO_2NR^3R^4$, $OCOR^5$, $SR^5$, $CO_2R^5$; $NHCOR^5$; or $R^1$, when disubstituted, can be taken together to form a 5, 6 or 7-membered carbocyclic aromatic group or heterocyclic aromatic group wherein the heterocyclic aromatic group is selected from the group consisting of furo, thieno, pyrido, pyrrolo, oxazolo, thiazolo, imidazolo, pyrazolo, isoxazolo, isothiazolo, pyridazino, pyrimidino, pyrazino, and indolo;

$R^2$ is branched or straight chain $C_1$–$C_6$ alkyl, $C_1$–$C_6$ alkoxy, a nitrogen-protected amino acid, phenyl, benzyl, $C_1$–$C_6$ alkenyl, hydroxy, $SO_2Ph$, $SO_2NR^3R^4$, $NR^3R^4$, $OCOR^5$, $SR^5$, $CO_2R^5$, $NHCOR^5$, or a heterocyclic aromatic group, whereby $R^2$ is unsubstituted or substituted;

$R_3$ and $R^4$ are independently hydrogen, $C_1$–$C_6$ alkyl or, taken together are $(CH_2)_f$ where f is 3–6;

$R^5$ is $C_1$–$C_6$ alkyl, benzyl, phenyl, or, substituted phenyl with 1–3 substituents independently selected from the group consisting of $C_1$–$C_6$ alkoxy, $NO_2$, $CF_3$, or CN; and Y is an appropriate cleavable linker such as —$NHCO_2CH_2$— or —O—$CH_2$, linked to a suitable solid support.

These compounds may possess antipyretic, hypotensive, antibacterial, antifungal or CNS activity, or the ability to inhibit enzymes of biological importance, such as metalloenzymes. The compounds may be any 3-hydroxy-4(1H)-quinazolinone, as described herein.

Preferred compounds are where $R^1$ is an independently selected mono-, di-, tri-, or quad-substituent on the phenyl ring, of a branched or straight $C_1$–$C_{10}$ alkyl, $C_4$–$C_{10}$ aryl, fluorine, chlorine, bromine, iodine, $NO_2$, $C_1$–$C_{10}$ alkoxy, $C_1$–$C_{10}$ alkenyl, $C_1$–$C_{10}$ aralkyl, $C_1$–$C_{10}$ aralkenyl, hydroxy, $SO_2Ph$, $SO_2NR^3R^4$, $NR^3R^4$, $OCOR^5$, $SR^5$, $CO_2R^5$, or $NHCOR^5$; and $R^2$ is a branched or straight $C_1$–$C_{10}$alkyl, $C_4$–$C_{10}$ aryl, $C_1$–$C_{10}$ alkoxy, $C_4$–$C_{10}$ aryloxy, $NHCO_2R^5$, $C_1$–$C_{10}$ alkenyl, hydroxy, $SO_2Ph$, $SO_2NR^3R^4$, $NR^3R^5$, $OCOR^5$, $SR^5$, $CO_2R^5$, $NHCOR^5$, or a 4–10 membered heterocyclic group; wherein $R^3$ and $R^4$ are independently hydrogen, a branched or straight $C_1$–$C_{10}$ alkyl, $C_4$–$C_{10}$ aryl, a halogen, $C_1$–$C_{10}$ alkoxy, $C_4$–$C_{10}$ aryloxy, $C_1$–$C_{10}$ alkenyl, $C_1$–$C_{10}$ aralkyl, $C_1$–$C_{10}$ aralkenyl, hydroxy, $SO_2Ph$, or $NH_2$.

More preferred compounds are those where $R^1$ is $C_1$–$C_8$ alkyl, $C_5$–$C_7$ aryl, fluorine, chlorine, bromine, iodine, or $NO_2$; and $R^2$ is $C_1$–$C_8$ alkyl, $C_5$–$C_7$ aryl, $NHCO_2R^5$, or a 5–7 membered heterocyclic aromatic compound selected from the group consisting of furo, thieno, pyrido, pyrrolo, oxazolo, thiazolo, imidazolo, pyrazolo, isoxazolo, isothiazolo, pyridazino, pyrimidino, pyrazino, and indolo.

Solid supports containing the N-amino- or N-hydroxy-4(1H)-quinazolinone group comprise a cleavable linker or linking arm which links the solid support to the compound. The linking arm is typically an oxygen-containing moiety that is cleavable by treatment with an organic or inorganic acid, thereby yielding the free N-amino- or N-hydroxy-4(1H)-quinazolinone. The library of compounds that can be generated on the solid support comprises a diverse array of substituted N-amino or N-hydroxy-4(1H)-quinazolinones, that once cleaved, can be screened to identify and/or isolate individual compounds that bind to a specific protein or receptor or possess some desired pharmacological or chemical property.

4. BRIEF DESCRIPTION OF THE DRAWINGS

FIG. 1 illustrates the synthesis of an N-hydroxy-quinazolinone of the present invention by preparing a 2-aminobenzamide on a solid support by reacting a hydroxylamine O-protected resin with an isatoic anhydride in the presence of an basic catalyst, and reacting the 2-aminobenzamide with an Fmoc-protected amino acid and removing the Fmoc protecting group to afford an amino-quinazolinone bound to the resin. The amino group can then either be (i) acylated with an acyl chloride in the presence of diisopropylethylamine or (ii) converted to a sulfonamide with a sulfonyl chloride in the presence of a diisopropyl-ethylamine or (iii) reacted with an Fmoc or t-Boc protected amino acid in the presence of a coupling agent to yield an amide or (iv) alkylated with an alkyl halide or (v) reacted with an isocyanate to form a urea. The products of (i), (ii), or (iii) above may be cleaved from the solid support under acidic conditions to yield an amino-substituted N-hydroxy-4(1H)-quinazolinone.

Figure 2:
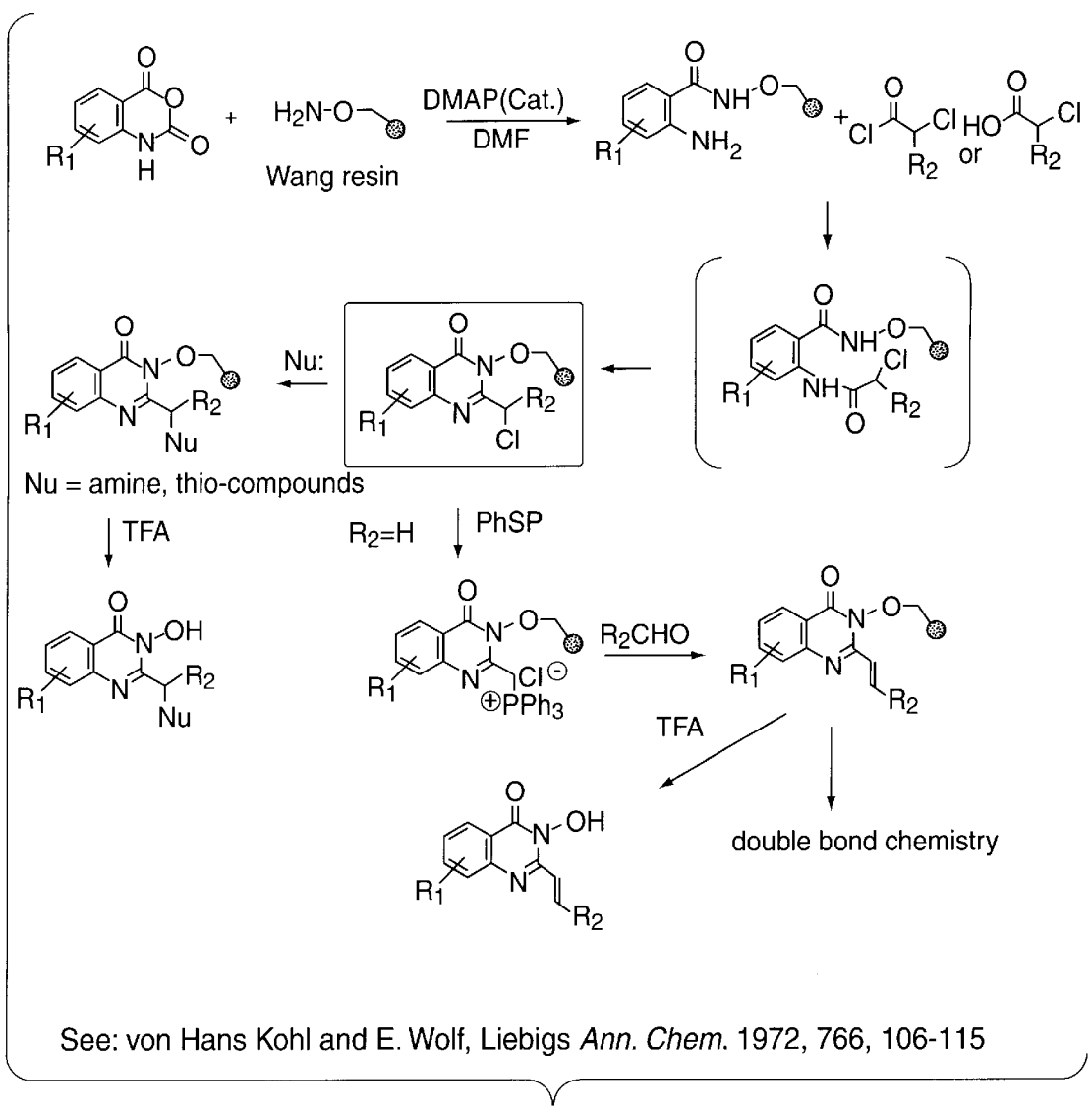

FIG. 2 illustrates the synthesis of 2-substituted N-hydroxy-quinazolinones of the present invention by preparing a 2-amino-benzamide on a solid support by reacting a hydroxylamine O-protected resin with an isatoic anhydride in the presence of a basic catalyst and reacting the 2-aminobenzamide with an alpha-halo acid chloride or an alpha-halo carboxylic acid. The corresponding alpha-halo-quinazolinone is (i) reacted with an appropriate nucleophile to displace the halide, such as an amine or sulfur nucleophile, yielding the substituted derivative or (ii)

reacted with triphenylphosphine to form the corresponding Wittig salt. The Wittig salt can then be reacted with an aldehyde or ketone to form a 2-alkenyl-quinazolinone. The products of (i) or (ii) above may be cleaved from the solid support under acidic conditions to yield the desired products.

Figure 3:
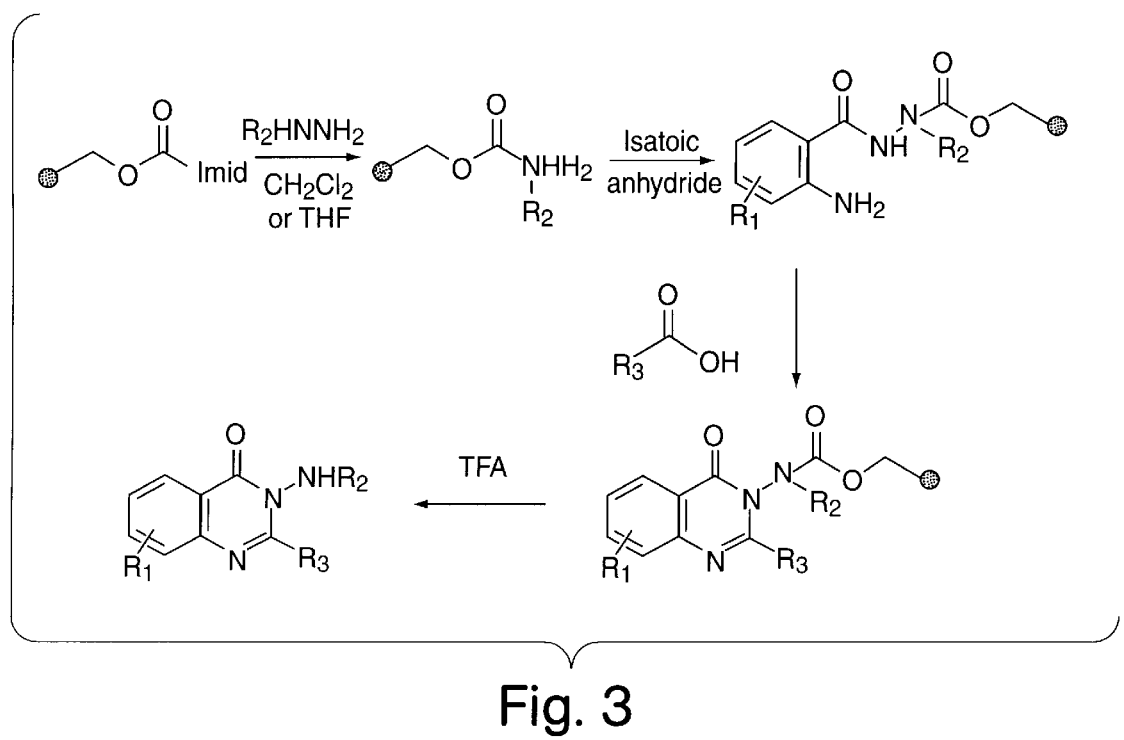

FIG. 3 illustrates the synthesis of 2-substituted N-aminoquinazolinones of the present invention by preparing a 1,2 disubstituted anthraniloylhydrazine on a solid support by reacting (1) the Wang resin with 1,1'-carbonyldiimidazole and (2) reacting the corresponding immidazolide with hydrazine to yield the carbazate and (3) reacting the carbazate with an isatoic anhydride in the presence of a basic catalyst such as dimethylaminopyridine. The 1,2 disubstituted anthraniloylhydrazine bound to the solid support is then reacted with the appropriate carboxylic acid in the presence of an appropriate coupling reagent such as bromotris-pyrrolidinophosphonium hexafluorophosphate (PyBrOP) to yield the corresponding 2-substituted-hydrazido-quinazolinones bound to the solid support. Cleavage from the solid support can be effected under acidic conditions to yield the corresponding N-aminoquinazolinones of the present invention.

Figure 4:
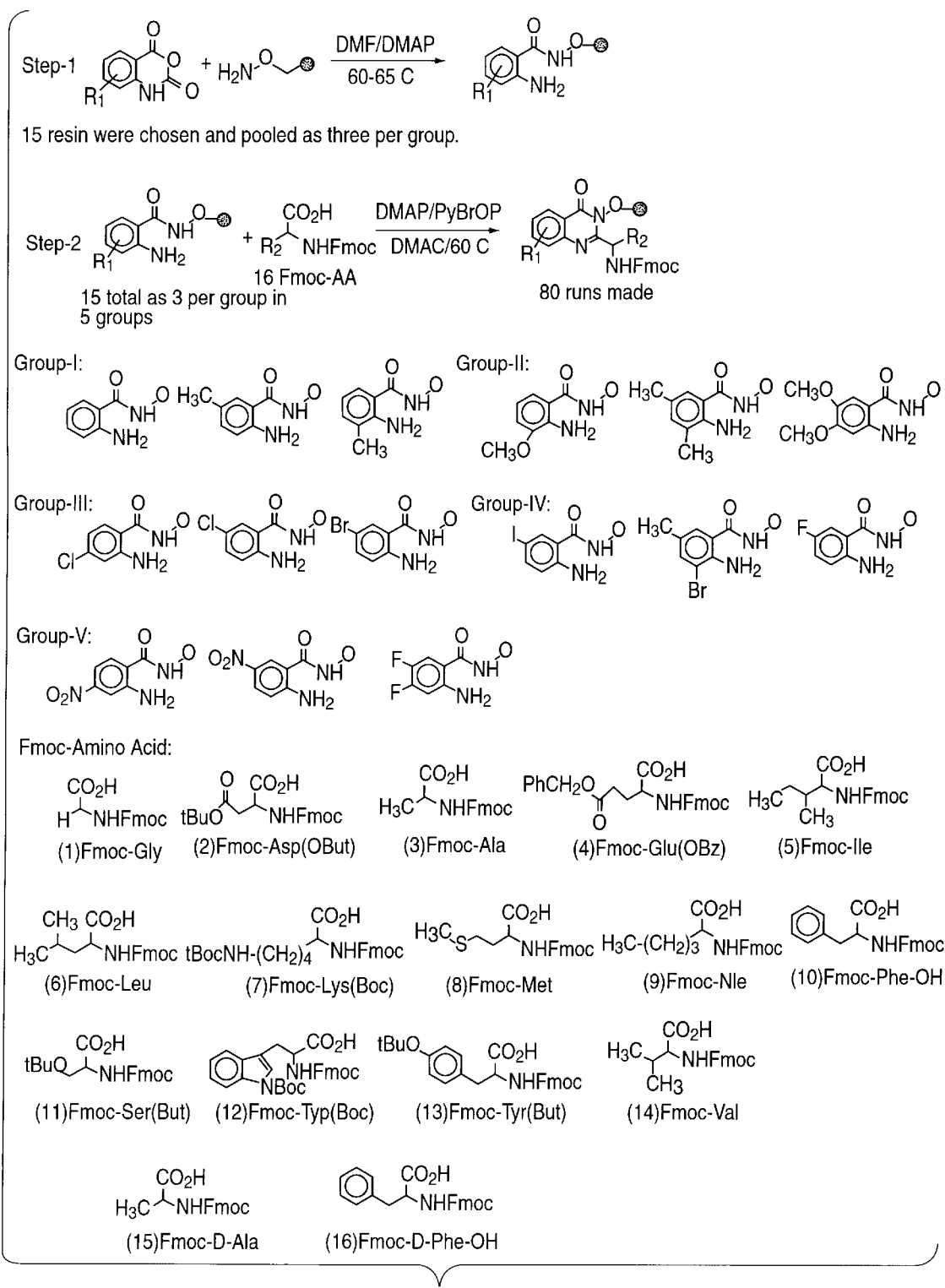
Figure 5:
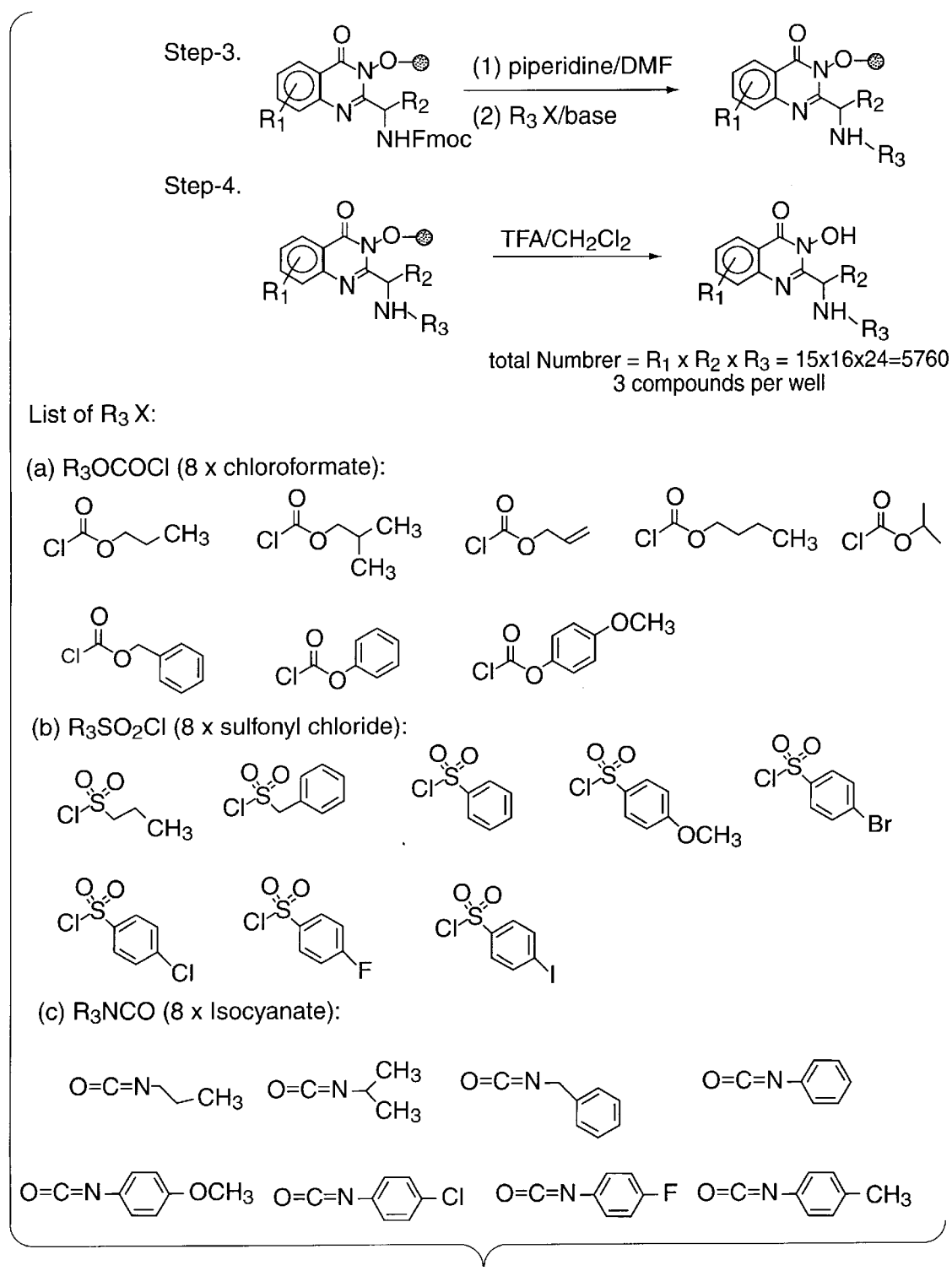

FIGS. 4 and 5 illustrate the preparation of a 5760-member library of 3-hydroxyquinazolinones by reacting a N-hydroxylamine on a Wang resin with fifteen isatoic anhydrides, followed by hydrolysis to the corresponding N-hydroxybenzamide. The fifteen N-hydroxybenzamides are divided into five groups and reacted with sixteen Fmoc-aminoacids, followed by cleavage of the Fmoc group to give eighty groups of free aminoquinazlinones on resins. Each of the 80 groups of resins are then evenly distributed into 24 wells of a reactor block. To each well is added eight chloroformates, eight sulfonyl chlorides and eight isocyanates yielding 1,920 wells of quinazolinones (3 compounds per well) as resins. The 1,920 wells of quinozolinanes were then treated with trifluoroacetic acid to remove the resin, yielding a library of 5,760 N-hydroxy quinazolinones.

5. DETAILED DESCRIPTION OF THE INVENTION

The present invention provides a reliable, high yielding synthetic method to prepare a large number of N-amino and hydroxy-4(1H)-quinazolinones via the base catalyzed cyclization of the appropriate 2-aminobenzamide with acyl halides or carboxylic acids under mild conditions. This reaction design facilitates purification, has high reliability and has high yield, which are achieved by use of a solid support as a protecting group. This solid-phase synthetic method also facilitates the assembly of combinatorial libraries of the N-amino- and N-hydroxy-4(1H)-quinazolinone pharmacophore, which permit rapid and efficient screening of tens, hundreds, and up to thousands of N-amino- and N-hydroxy-4(1H)-quinazolinones for pharmacological activity. The solid-phase or resin bound molecules can also be further substituted or simply isolated and screened.

Generally, the compounds of this invention are organic compounds where the serial synthesis involves the addition or removal of chemical units, reactions involving the modification or introduction of one or more functionalities, ring openings, ring closings, etc. Chemical units can take many forms, both naturally-occurring and synthetic, such as nucleophiles, electrophiles, dienes, alkylating or acylating agents, diamines, nucleotides, amino acids, sugars, lipids, or derivatives thereof, organic monomers, and combinations thereof. Alternatively, reactions may be involved that result in alkylation, acylation, nitration, halogenation, oxidation, reduction, hydrolysis, substitution, elimination, addition, and the like.

In some instances, one may wish to have the same or different blocks introduced at the same or different stages. For example, one may wish to have a common functional unit, e.g., a 2-aminobenzamide introduced during the synthesis. In this manner one may achieve a molecular context into which the variation is introduced. These situations may involve only a few stages having a plurality of choices, where a large number of products are produced in relation to a particular functional entity. This could have particular application where one is interested in a large number of derivatives related to a core molecule or unit known to have a characteristic of interest, and advantageously permits formation of an array, or library, of compounds.

In developing synthetic strategies, one can provide for batch synthesis of a few compounds to be prepared during the course of the combinatorial synthesis. For example, such as syntheses involving steric hindrance, charge and/or dipole interactions, alternative reaction pathways, or the like, one can optimize conditions to provide for enhanced yields of compounds that might not otherwise be formed or be formed only in low yield. In this manner, one may allow for a variety of reaction conditions during the combinatorial synthesis, involving differences in solvent, temperatures, times, concentrations, and the like. Furthermore, one may use batch synthesis, which will provide much higher concentrations of particular products than combinatorial synthesis, to develop assays to characterize the activity of the compounds.

The invention further relates to a combinatorial library of compounds comprising q different compounds, wherein each of the compounds is prepared according to the methods discussed above having the Formula (II) comprising:

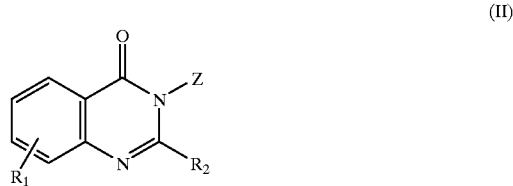

(II)

wherein q is an integer greater than 1 which represents the total number of molecules in the library. In a preferred embodiment, each compound in the library is novel.

The invention also relates to an "m times p" array of molecules comprising q compounds having the Formula (II).

wherein at least q molecules in said array have at least one different structural group; and wherein $R^1$ is an independently selected mono-, di-, tri-, or quad-substituent on the phenyl ring, and where $R^1$ is independently hydrogen, halogen, $C_1$–$C_6$ alkyl, $C_1$–$C_6$ alkenyl, hydroxy, $C_1$–$C_6$ alkoxy, $NO_2$, $SO_2Ph$, phenyl, $SO_2NR^3R^4$, $OCOR^5$, $SR^5$, $CO_2R^5$; $NHCOR^5$; or $R^1$, when disubstituted, can be taken together to form a 5, 6 or 7 membered carbocyclic aromatic group or heterocyclic aromatic group wherein the heterocyclic aromatic group is selected from the group consisting of furo, thieno, pyrido, pyrrolo, oxazolo, thiazolo, imidazolo, pyrazolo, isoxazolo, isothiazolo, pyridazino, pyrimidino, pyrazino, and indolo;

$R^2$ is branched or straight chain $C_1$–$C_6$ alkyl, $C_1$–$C_6$ alkoxy, a nitrogen-protected amino acid, phenyl, benzyl, $C_1$–$C_6$ alkenyl, hydroxy, $SO_2Ph$, $SO_2NR^3R^4$, $NR^3R^4$, $OCOR^5$, $SR^5$, $CO_2R^5$, $NHCOR^5$, or a heterocyclic aromatic group, whereby $R^2$ is unsubstituted or substituted.

$R^3$ and $R^4$ are independently hydrogen, $C_1$–$C_6$ alkyl or, taken together are $(CH_2)_f$ where f is 3–6;

$R^5$ is $C_1$–$C_6$ alkyl, benzyl, phenyl, or, substituted phenyl with 1–3 substituents independently selected from the group consisting of $C_1$–$C_6$ alkoxy, $NO_2$, $CF_3$, or CN; and Z is OH or $NHR^2$;

m is an integer greater than 0;

p is an integer greater than 1 and greater than m;

and q is an integer greater than 1.

Preferably, the array is such that m and p are each an integer between 1 and 25, and q is equal to m multiplied by p. The invention also relates to an m times p array of compartments containing these molecules.

The invention also includes pharmaceutical compositions including these compounds, and methods of administering a therapeutically effective amount of the pharmaceutical compositions, or a pharmaceutically acceptable salt thereof. Such pharmaceutical compositions and methods of administering the same are discussed further herein. These pharmaceutical compositions include the compounds discussed herein in a pharmaceutically acceptable format. Typically, this includes a pharmaceutically acceptable carrier and a therapeutically effective amount of the N-hydroxyquinazolinone compound, or a pharmaceutically acceptable salt thereof.

The present invention also relates to a solid phase reaction component comprising a solid support substantially insoluble in aqueous or organic reaction media, carrying a plurality of covalently bound hydroxylamines available for reaction with the substrate.

Suitable solid supports include those known in the art of solid phase synthesis. Some known supports, for example, are described in J. Stewart and J. Young (*Solid Phase Peptide Synthesis*, 2nd Ed., Pierce Chemical Company; Rockford, Ill., 1984), which is incorporated herein by reference thereto. They include inorganic substrates, for example, kieselguhr, silica gel and controlled pore glass, and polymeric organic substrates, for example, polystyrene, polypropylene, polethyleneglycol, polyacrylamide, cellulose, as well as composite inorganic/polymeric substrates, such as polyacrylamide supported within a matrix of kieselguhr particles. Such known solid supports include carboxy and acyl halide functionalized solid supports, such as those which are chemically modified by introduction of carboxylic acid or acyl halide groups, to serve as convenient points for further chemical manipulation.

The solid phase reaction components of the present invention include a solid support, as described above, and a clearable linker or linker arm which presents the carboxylic acid or acyl halide moiety of the hydroxamate group for reaction with the first reactive entity in the proposed synthesis.

As used in this application, the term "linker" means a chemical moiety which may possess a variety of properties. First, it is attachable to a solid support. Second, it is cleavable from the solid support such that when it is cleaved, the desired compound may be released from the solid support. These properties may be embodied by a single chemical structure. Alternatively, these properties may be embodied in multiple chemical structures which are linked together by covalent bonds or by other means.

When detachment of the product from the solid support is desired, there are numerous functionalities and reactants which may be used. Conveniently, ethers may be used, where substituted benzyl ether or derivatives thereof, e.g., benzhydryl ether and indanyl ether, may be cleaved by acidic or mild reductive conditions. Alternatively, one may employ β-elimination, where a mild base may serve to release the product. Acetals, including the thio analogs thereof, may be employed, where mild acid, particularly in the presence of a capturing carbonyl compound, is preferred. By combining formaldehyde, HCl, and an alcohol moiety, an α-chloroether is formed. This chloroether may then be coupled with an hydroxy functionality on the solid support to form the acetal. Various photolabile linkages may be employed, such as o-nitrobenzyl, 7-nitroindanyl, 2-nitrobenzhydryl ethers or esters, for example. Esters and amides may serve as linkers, where half-acid esters or amides are formed, particularly with cyclic anhydrides, followed by reaction with hydroxyl or amino functionalities on the solid support, using a coupling agent such as a carbodiimide. Peptides may be used as linkers, where the sequence is subject to enzymatic hydrolysis, particularly where the coenzyme recognizes a specific sequence. Carbonates and carbamates may be prepared using carbonic acid, base or a strong reductant, e.g., $LiAlH_4$, particularly for the carbonate esters. Suitable cleavable linkers are disclosed in Greene and Wuts (*Protective Groups in Organic Synthesis*, 2nd ed. Wiley, 1991), which is incorporated herein in its entirety by reference thereto. The versatility of the various systems allows for broad variation in the conditions for attachment of products and identifiers and differential detachment of desired products.

5.1. Solid-Phase Synthesis of N-Amino and N-Hydroxy-Quinazolinones

A preferred embodiment of this invention is a solid phase reaction component on a solid support, which is substantially insoluble in an aqueous or organic reaction media, carries a plurality of groups of a compound of Formula (I):

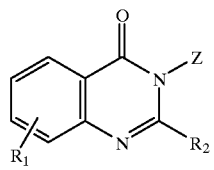

wherein $R^1$ is an independently selected mono-, di-, tri-, or quad-substitutent on the phenyl ring, and where $R^1$ is independently hydrogen, halogen, $C_1$–$C_6$ alkyl, $C_2$–$C_6$ alkenyl, $C_2$–$C_6$ alkynyl optionally substituted with halogen, hydroxy, $C_1$–$C_6$ alkoxy and aryl, or hydroxy, $C_1$–$C_6$ alkoxy, $NO_2$, $SO_2Ph$, phenyl, $SO_2NR^3R^4$, $OCOR^5$, $SR^5$, $CO_2R^5$; $NHCOR^5$; or $R^1$, when disubstituted, can be taken together to form a 5–7 membered carbocyclic aromatic group or heterocyclic aromatic group wherein the heterocyclic aromatic group is selected from the group consisting of furo, thieno, pyrido, pyrrolo, oxazolo, thiazolo, imidazolo, pyrazolo, isoxazolo, isothiazolo, pyridazino, pyrimidino, pyrazino, and indolo;

$R^2$ is branched or straight chain $C_1$–$C_6$ alkyl, $C_1$–$C_6$ alkoxy, a nitrogen-protected amino acid, phenyl, benzyl, $C_1$–$C_6$ alkenyl, hydroxy, $SO_2Ph$, $SO_2NR^3R^4$, $NR^3R^4$, $OCOR^5$, $SR^5$, $CO_2R^5$, $NHCOR^5$, or a heterocyclic aromatic group, whereby $R^2$ is unsubstituted or substituted;

$R^3$ and $R^4$ are independently hydrogen, $C_1$–$C_6$ alkyl or, taken together are $(CH_2)_f$ where f is 3–6;

$R^5$ is $C_1$–$C_6$ alkyl, benzyl, phenyl, or, substituted phenyl with 1–3 substituents independently selected from the group consisting of $C_1$–$C_6$ alkoxy, $NO_2$, $CF_3$, or CN; and Y is an appropriate cleavable linker such as —$NHCO_2CH_2$— or —O—$CH_2$—, linked to a suitable solid support.

A preferred group of solid phase reaction components are those where $R^1$ is a branched or straight $C_1$–$C_{10}$ alkyl, $C_4$–$C_{10}$ aryl, fluorine, chlorine, bromine, iodine, $NO_2$, $C_1$–$C_{10}$ alkoxy, $C_1$–$C_{10}$ alkoxy, $C_1$–$C_{10}$ alkenyl, $C_1$–C alkaryl, $C_1$–$C_{10}$ aralkenyl, hydroxy, $SO_2Ph$, $SO_2NR^3R^4$, $OCOR^5$, $SR^5$, $CO_2R^5$, or $NHCOR^5$; and $R^2$ is a branched or straight $C_1$–$C_{10}$ alkyl, $C_4$–$C_{10}$ aryl, $C_1$–$C_{10}$ alkoxy, $C_4$–$C_{10}$ aryloxy, $NHCO_2R^5$, $C_1$–$C_{10}$ alkenyl, $C_1$–$C_{10}$ aralkyl, $C_1$–$C_{10}$ aralkenyl, hydroxy, $SO_2Ph$, $SO_2NR^3R^4$, $OCOR^5$, $SR^5$, $CO_2R^5$, $NHCOR^5$, or a 4–10 membered heterocyclic group.

A more preferred group of solid phase reaction components are those where $R^1$ is $C_1$–$C_6$ alkyl, $C_2$–$C_6$ alkynyl optionally substituted with halogen, hydroxy, $C_1$–$C_6$ alkoxy and $C_5$–$C_7$ aryl, fluorine, chlorine, bromine, iodine, or $NO_2$; and $R^2$ is $C_1$–$C_6$ alkyl, aryl, $NHCO_2R^5$, or a 5–7 membered heterocyclic aromatic compound selected from the group consisting of furo, thieno, pyrido, pyrrolo, oxazolo, thiazolo, imidazolo, pyrazolo, isoxazolo, isothiazolo, pyridazino, pyrimidino, pyrazino, and indolo.

In this embodiment, precursor compounds of the Formula (I) are linked to the solid support via a cleavable linker, i.e., the oxygen. It will be apparent that the cleavable linker may be incorporated during synthesis of the solid phase reaction component of the invention by starting with a preferred solid support, such as hydroxymethyl polystyrene, 4-(Hydroxymethyl)phenoxymethyl-copoly(styrene-1% divinylbenzene)-resin (100–200 mesh, "WANG" resin), hydroxymethyl copoly(styrene-1% divinylbenzene), benzhydrylaminepolystyrene, benzhydrylamine copoly (styrene-1% divinylbenzene (commercially available as "BHA Resin"), methyl benzhydryl aminepolystyrene, methyl benzhydrylamine copoly(styrene-1% divinylbenzene (commercially available as "MBHA Resin"); polyethylene glycol polystyrene ("PEG-PS"); poly (dimethylacrylamide)polystyrene composite (commercially available as "POLYHIPE"); polyacrylamide Kieselguhr composite (commercially available as "MACROSORB"); or functionalized controlled pore glass. The preferred solid supports are Wang Resin and the BHA resin. A more preferred solid phase reaction component of the present invention uses 4-(hydroxymethyl)-phenoxymethylcopoly (styrene-1divinylbenzene)-resin (100–200 mesh, "WANG" resin) as the solid support.

The solid-phase reaction components of the invention will generally be accessible (i) by displacement of the hydroxyl group on the solid support by N-hydroxyphthalimide in the presence of triphenyl phosphine and diethyl azodicarboxylate or by displacement of a leaving group (e.g. mesylate or triflate) with N-hydroxyphthalimide in the presence of a strong base (e.g. sodium hydride) followed by (ii) removal of the phthalimide protecting group with hydrazine hydrate affording an O-solid supported N-hydroxylamine.

The amine moiety of the O-solid supported N-hydroxyl amine is then reacted with a diverse array of isatoic anhydrides to produce the corresponding 2-amino-hydroxybenzamides bound to the solid support. The isatoic anhydrides are either commercially available from, for example, Aldrich Chemical Co. or may be generally synthesized from the reaction of a diverse array of anthranilic acids with triphosgene in tetrahydrofuran at room temperature followed by cooling to 0° C. to precipitate the desired isatoic anhydride. For example, treatment of the isatoic anhydride with the O-solid supported N-hydroxyl amine in the presence of a basic catalyst such as dimethylaminopyridine (DMAP) in dry dimethylformamide at about 60–70° C. for about 24–60 hours afforded the corresponding 2-amino-N-alkoxybenzamide on the solid support.

The invention further relates to methods for preparing derivatives of the N-hydroxy-4(1H)-quinazolinones on a solid phase reaction component, including a solid support that is substantially insoluble in aqueous or organic reaction media. This method is the preferred synthetic route, and in one embodiment (Scheme I) involves the following steps:

Scheme I

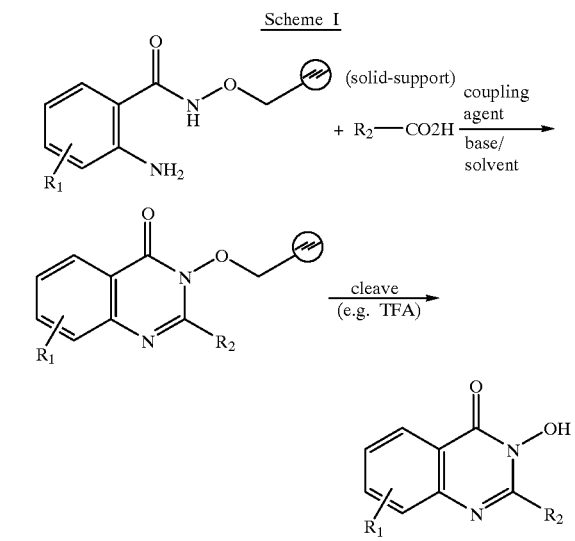

wherein $R^1$ and $R^2$ are as described above for the compounds of Formula (I).

In Scheme I, a 2-aminobenzamide bound to a solid support is reacted with a carboxylic acid ($R^2CO_2H$) in the presence of a coupling agent, base, and solvent to yield a N-alkoxy-4(1H)-quinazolinone bound to the solid support. The 2-aminobenzamide is produced via the reaction of the amino group of hydroxylamine bound to the solid support through an ether linkage with an isatoic anhydride. The desired N-hydroxy-4(1H)-quinazolinone can be cleaved from the solid support under acidic conditions.

In a further embodiment, when the 2-aminobenzamide is reacted with an N-protected amino acid in the presence of a basic catalyst and a coupling agent, a N-alkoxyquinazolinone bearing an amino acid substituent is formed. The coupling reaction and subsequent cyclization can be conveniently performed in an aprotic organic solvent such as dimethylformamide or dimethylacetamide in the presence of a basic catalyst such as dimethylaminopyridine. An appropriate coupling agent is bromo-tris-pyrrolidino-phosphonium hexafluorophosphate (PyBrOP). Another suitable coupling agent is Tris-pyrrolidino-phosphonium hexafluorophosphate (PyBOP).

The quinazolinone bearing the N-protected amino acid bound to the solid support can be deprotected under standard conditions depending upon the protecting group employed. Appropriate protecting groups for amino acids and conditions for their removal can be formed in Greene and Wuts, Protective Groups in Organic Synthesis, 2nd Ed. Wiley, 1991. The amino-quinazolinone can the be derivatized to give amides, sulfonamides, ureas or peptides. Treatment of the amino-quinazolinone with an acid chloride or a chloroformate in the presence of a base, such as diisopropylethylamine, yields an amide or carbamate derivative of a quinazolinone bound to the solid support. Furthermore, treatment of the aminoquinazolinone with an isocyanate provides the urea derivative of a quinazolinone bound to the solid support. Alternatively, treatment of the amino-quinazolinone with a sulfonyl chloride in the presence of diisopropylethylamine yields a sulfonamide derivative of a quinazolinone bound to a solid support. Other bases that are suitable for effecting this transformation include, but are not limited to, diisopropylethylamine, dimethylaminopyridine, triethylamine, or pyridine. In a further embodiment, the amino-quinazolinone may be further reacted with another N-protected amino acid to yield a peptidyl derivatized of a quinazolinone bound to a solid support. The derivated compounds can then be removed from the solid support under acidic conditions. Aqueous trifluoroacetic acid (TFA), or a mixture of trifluoroaectic acid and an organic solvent, will generally be suitable for the acid hydrolysis of the covalent bond between the derivatized quinazolinones and the solid support.

Alternatively, an $R_2$ acyl halide may be used in place of the $R_2$ carboxylic acid. In a further embodiment, reaction of a 2-aminobenzamide bound to a solid support with an alpha-halo acid chloride or alpha-halo carboxylic acid yields the corresponding 2-alpha-halo quinazolinone. The halo derivative is (i) reacted with an appropriate nucleophile, such as an amine or sulfur nucleophile, to displace the halide or (ii) reacted with triphenylphosphine to form the corresponding Wittig salt. The Wittig salt can then be reacted with an aldehyde or ketone under standard Wittig conditions to form a 2-alkenyl quinazolinone. The products of (i) and (ii) above may be cleaved from the solid support under acidic conditions to yield the desired products. Several examples disclosed herein, as well as FIGS. 1 & 2, indicate alternative routes to synthesize the N-hydroxy-quinazolinones of the present invention.

The preferred method for synthesizing N-hydroxyquinazolinones involves cyclizing a 2-aminobenzamide on a solid support by reaction with a carboxylic acid in the presence of an activating agent and a base or reaction with an acyl halide in the presence of a base, and cleaving the product from said solid support.

In a preferred form, the N-hydroxy-quinazolinone is a 3-hydroxy-4(1H)-quinazolinone or a derivative thereof. It is also preferable to react the 2-aminobenzamide on the solid support and the carboxylic acid in the presence of an activating agent in the presence of at least one solvent selected from the class of aprotic organic solvents, and it is preferable to cleave the N-hydroxyquinazolinone from the solid support under acidic conditions.

The invention further relates to methods for preparing of the N-amino-4(1H)-quinazolinones on a solid phase reaction component, including a solid support that is substantially insoluble in aqueous or organic reaction media. This method is the preferred synthetic route, and in one embodiment (Scheme II) involves the following steps:

Scheme II

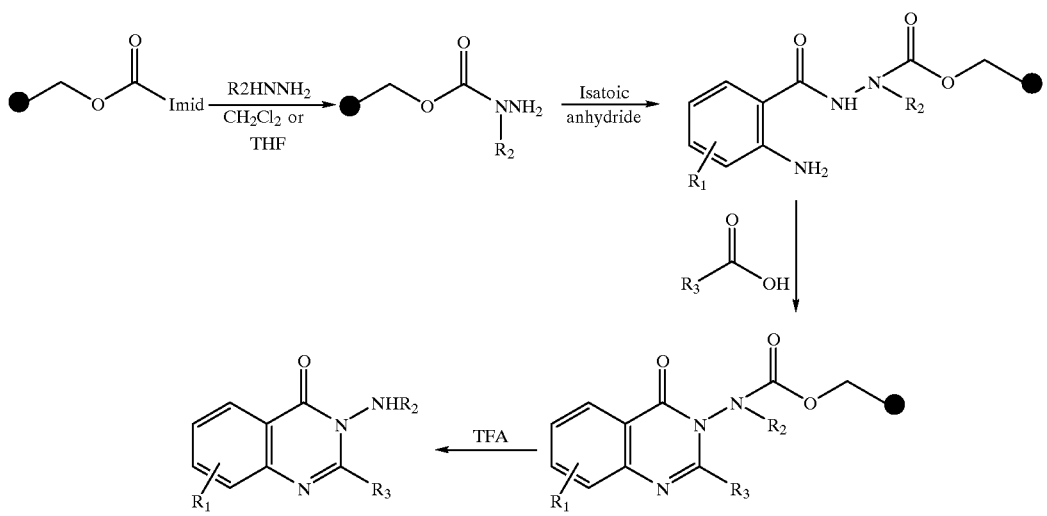

wherein $R^1$ and $R^2$ are as described for the compounds of Formula (I).

In Scheme II, an imidazolide prepared from reacting a hydroxyl resin with carbonyldiimidazole is reacted with hydrazine to produce a carbazate. The carbazate is reacted with an isatoic anhydride in the presence of a basic catalyst, such a dimethylaminopyridine, to yield the corresponding 1,2 disubstituted anthraniloyl hydrazine on the solid phase. The anthraniloyl hydrazine on the solid phase in reacted with a carboxylic acid in the presence of a coupling agent, base, and solvent to yield and N-hydrazino-4(1H)-quinazolinone bound to the solid support. The desired N-amino-4(1H)-quinazolinone can be cleaved from the solid support under acidic conditions.

As used herein the term "$C_1$–$C_6$ alkyl" means a straight or branched chain alkyl moiety having from 1 to 6 atoms, including, for example, methyl, ethyl, n-propyl, isopropyl, n-butyl, isobutyl, sec-butyl, t-butyl, pentyl and hexyl. The term "$C_1$–$C_6$ alkoxy" means an alkoxy group wherein the alkyl part is $C_1$–$C_6$ alkyl. The terms "$C_1$–$C_{10}$ alkyl" and "$C_1$–$C_{10}$ alkoxy" are the same, except for having 1 to 10 atoms.

The term "halogen" means fluorine, bromine, iodine, or chlorine. The term "$C_1$–$C_6$ aralkyl" means a straight or branched chain alkyl moiety having from 1–6 atoms bearing a phenyl substituent at any carbon in the chain. The term "$C_1$–$C_6$ aralkenyl" means a straight or branched chain alkenyl moiety having from 1–6 atoms bearing a phenyl substituent at any carbon in the chain. The terms "$C_1$–$C_{10}$ aralkyl" and "$C_1$–$C_{10}$ aralkenyl" are the same, except for having 1 to 10 atoms.

The choice of solvent for synthesis based on a solid phase reaction component of the invention will of course depend on the nature of the reagents to be reacted with such component, but will also be influenced by the nature of that component. For example, depending upon the activating group of acyl halide or carboxylic acid used in the formation of compounds of Formula (I), the selected solvent will vary according to the solubility of the selected activating group. In general, aprotic organic solvents are most suitable for the formation of compounds of the Formula (I).

Preferred solvents include dimethylformamide, dimethylacetamide, or N-methyl pyrrolidinone. The formation of compounds of Formula (I) bound to the solid support from $R_2CO_2H$ is conducted in the presence of an appropriate activating agent such as PyBrOP.

The compounds of the present invention are typically used in pharmaceutical compositions, a discussion of which follows. These pharmaceutical compositions are generally used in methods for administering a therapeutically effective amount of the compositions of the invention, or a pharmaceutically acceptable salt thereof.

The pharmaceutical compositions used in the methods of the present invention include N-hydroxyquinazolinone as an active ingredient, or a pharmaceutically acceptable salt thereof, and may also contain a pharmaceutically acceptable carrier or excipient, and optionally, other therapeutic ingredients.

6. EXAMPLES

The following examples are set forth to illustrate the claimed invention and are not to be construed as a limitation thereof.

Unless otherwise stated, all temperatures are in degrees Celsius. Also, in these examples, unless otherwise defined below, the abbreviations employed have their generally accepted meaning:

| | | |
|---|---|---|
| mL | = | milliliter |
| RT | = | room temperature |
| mmol | = | millimole |
| THF | = | tetrahydrofuran |
| DMF | = | dimethylformamide |
| DMAP | = | dimethylaminopyridine |
| TFA | = | trifluoroacetic acid |
| EtOAc | = | ethyl acetate |
| PyBrOP | = | bromo-tris-pyrrolidino-phosphonium hexafluorophosphate |
| DMAC | = | dimethylacetamide |

Additionally, the Wang Resin described herein and in FIGS. 1 and 2 is commercially available from Aldrich Chemical Co., Milwaukee, Wis. Also, the isatoic anhydrides described herein are commercially available from Aldrich Chemical Co. or may be synthesized according to the procedures described herein.

Example 1

General Procedure to Prepare Isatoic Anhydrides

An ice-cold solution of triphosgene (3.0 g, 10 mmol, 0.4 eq) in 10 mL of anhydrous THF was added to a mixture or solution of anthranilic acid (or 2-amino-benzoic acid) (25 mmol) in 15 mL of dry THF with slow cooling. The mixture was then stirred or shaken for 24–48 h at room temperature and cooled in a refrigerator (0° C. to –10° C.) for 12–24 h. The resulting solid was collected by filtration and washed with cold methyl t-butyl ether (MTBE) and dried to give the isatoic anhydride in 70–98% yield. About 30 isatoic anhydrides were prepared in this manner.

Example 1(a)

Preparation of O-Solid Supported N-hydroxylamine on Wang Resin

Triphenyl phosphine (28.2 g, 108 mmol) was dissolved in 300 mL of dry THF. To the solution was added Wang resin (25 g, 0.86 mmol/g loading, 100–200 mesh) and N-hydroxyphthalimide (18 g, 108 mmol). The mixture was shaken until most of the N-hydroxyphthalimide was dissolved. The mixture was then cooled with ice-water and a cold solution of diethyl azodicarboxylate (17 mL, 108 mmol) in 20 mL of dry THF was added slowly with shaking and cooling. After addition, the resulting mixture was shaken at rt for 18 h. The mixture was then washed with THF, DMF, $CH_3OH$ and $CH_2Cl_2$ thoroughly. The washed resin was then suspended in 300 mL of DMF and cooled with ice-water. Hydrazine hydrate (27 mL, 540 mmol) was then added. The mixture was shaken at rt for 16 h and then washed with DMP, $CH_3OH$ and $CH_2Cl_2$ thoroughly and dried under vacuum to give the O-resin supported hydroxylamine (ca 25 g).

Example 2

General Procedure for Reaction of Isatoic Anhydride with Solid-Supported Hydroxylamine A mixture of an isatoic anhydride (3.6 mmol) and O-hydroxylamine on Wang resin (0.6 g, 1.19 mmol/g loading) and DMAP (0.18 mmol) in ca. 8–10 mL of dry DMF was stirred at 60–70° C. for 2.5 days. The mixture was then washed with DMF, $CH_3OH$ and $CH_2Cl_2$ to give O-resin supported 2-amino-N-hydroxylbenzamide. A sample of the resin was cleaved with trifluoroacetic acid (TFA) in $CH_2Cl_2$ (1:1 v/v) to give the corresponding 2-amino-N-hydroxybenzamide to confirm the attachment to the resin.

Example 3

General Procedure for Cyclization of 2-amino-N-hydroxybenzamide on Solid-Support With Fmoc Amino Acid Fmoc-amino acid (6.0 eq) and PyBrOP (5.0 eq) is dissolved in DMAC (0.3 M of Fmoc-AA conc.) at RT. The 2-amino-N-hydroxybenzamide on Wang resin (1.0 eq based on loading) is added, followed by DMAP (6.0 eq). The mixture is shaken at 50° C. for 8–20 h (followed by HPLC/MS after cleavage of a small sample by TFA/$CH_2Cl_2$). The resin is then washed with DMF, MeOH and $CH_2Cl_2$ and dried under vacuum to give the corresponding quinazolinone on solid support. The Fmoc group can be removed by piperidine in DMF to give the free amino group which can react with other reagents, such as acid chloride, sulfonyl chloride or Fmoc or t-Boc amino acid. This synthesis is illustrated in FIG. 2.

Examples 4–6

Preparation of 3-hydroxy-quinazolinones via Solid-Support (a) (L)-N-Fmoc-phenylalanine (70 mg, 0.18 mmol) is dissolved in 0.7 mL of dry DMAC. PyBrOP (84 mg, 0.18 mmol) is added. The mixture is shaken for 10 min until a clear solution is formed. 2-amino-N-hydroxybenzamide on Wang resin (linked via the N-hydroxyl group) (30 mg, 1.19 mmol/g loading, 0.036 mmol) is added followed by DMAP (22 mg, 0.18 mmol). The mixture is shaken at RT. for 21 h and 50° C. for 3 h. (A sample is cleaved by TFA/$CH_2Cl_2$ and analyzed by HPLC to confirm the completion of the reaction). The mixture was cooled and washed with DMF, MeOH and $CH_2Cl_2$ thoroughly and dried to give N-Fmoc protected quinazolinone on resin.

The above resin is then treated with 30% piperidine in DMF to remove the N-Fmoc group to give the free amino group on the sidechain.

The above resin (30 mg, 1.19 mmol/g loading) was treated with p-bromobenzenesulfonyl chloride (37 mg, 0.143 mmol) and diisopropylethylamine (DIPEA) (0.038 mL, 0.22 mmol) in the presence of 5 mg of DMAP in 0.5 mL of DMF at RT. for 19 h. The resulting resin was then washed with DMF, MeOH and $CH_2Cl_2$ and dried.

The resin was then treated with TFA/$CH_2Cl_2$ (1:1, 0.5 mL) to give 2-(2-phenyl-1-p-bromobenzenesulfonamido)ethyl-3-hydroxyquinazolinone as confirmed by HPLC and MS analysis.

(b) In a similar manner, 5-chloro-2-amino-N-hydroxybenzamide on resin was treated with Fmoc-phenylalanine followed by removal of the N-Fmoc group by piperidine. The resulting free amino quinazolinone on resin was then treated with isobutylchloroformate (0.018 mL, 0.14 mmol) and DIPEA (0.038 mL, 0.22 mmol) in DMF. After 19 h at RT., the resin was washed with DMF, MeOH and $CH_2Cl_2$ as usual. The resin was then cleaved with TFA/$CH_2Cl_2$ to give 2-(2-phenyl-1-O-isobutylcarbonyl)ethyl-3-hydroxyquinazolinone.

(c) In a similar manner, 5-nitro-2-amino-N-hydroxybenzamide on resin was treated with Fmoc-(L)-valine followed by removal of the N-Fmoc group by piperidine. The resulting amino quinazolinone on resin (30 mg, 0.036 mmol based on loading) was then treated with t-Boc-proline (31 mg, 0.14 mmol) and PyBrOP (67 mg, 0.14 mmol) and DMAP (18 mg, 0.15 mmol) to give the coupled product. Cleavage with TFA/$CH_2Cl_2$ then gave 2-(2-methyl-1-N-Pro-)propyl-3-hydroxy-6-nitroquinazolinone.

Example 7

Preparation of 3-amino-quinazolinones via Solid-Support (1) Preparation of Carbazate on Solid Phase Wang resin (0.9 g, 1.19 mmol/g) was suspended in 10 mL of dry THF at room temperature. 1,1'-carbonyldiimidazole (1.1 g, 6.5 mmol) was added and the mixture was shaken on a shaker overnight. The resin was filtered, washed with THF, CH2Cl2 (2×20 mL each) and vacuum dried to give the corresponding imidazolide (0.9 g) (ref. J. r. Hauske, et al. Tet. Lett. 1995, 36,1589).

The above resin (0.9 g) was suspended in 6 mL of THF and cooled with ice water. A solution of Hydrazine (0.138 g, 4.28 mol) in 1 mL of THF was added. The suspension as then shaken at room temperature for 2–3 h and filtered and washed with THF and CH2Cl2 (2×20) mL each) and dried to give the carbazate on solid phase.

(2) General Procedure for Reaction of Isatoic Anhydride With Carbazate on Solid Phase The carbazate on the solid phase from above (50 mg, 1.19 mmol/g) was suspended in 0.6 mL of dry DMF. Isatoic anhydride (0.3 mmol, 5.0 eqq) isatoic anhydrides used: 5-chloroisatoic anhydridge, 5-iodoisatoic anhydride and isa-toic anhydride) and a catalytic amount of DMAP were added, the mixture was heated at 50–60 C. with stirring overnight (12–18 h). The resin was filtered and washed with DMF, Me)H, and CH2Cl2 (2×10 mL each) and dried under vacuum to give the corresponding 1,2-disubstituted anthraniloylhydrazine on solid phase.

(3) Preparation of N-amino-quinazolinones From Anthraniloylhydrazine on Solid Phase (a) 5-bromo indole carboxylic acid (109 mg, 0.43 mmol) and PyBroP (173 mg, 0.37 mmol) were dissolved in 0.6 mL of DMF. The anthraniloylhydrazine on solid phase (45 mg, 1.19 mmol/g) was added followed by DMAP (58 mg, 0.48 mmol). The mixture was shaken at room temperature for 20–30 min and then was heated at 55–60 C. for 18 h. The resin was filtered and washed with DMF, MeOH, CH2Cl2 (2×5 ml each) and dried. The produce on resin was then cleaved with 0.5 mL of TFA/CH2Cl2 (1:1, v/v) to give the N-aminoquinazolinone as a yellowish solid (10 mg) (M+495 by mass spec).

(b) Fmoc-phenylalanine (138 mg, 0.36 mmol) and PyBrOP (140 mg, 0.3 mmol) were dissolved in 0.6 mL of DMF. The anthraniloylhydrazine (R1-H and R1-5Cl) (50 mg., 1.19 mmol/g) was added followed by DMAP (51 mg, 0.42 mmol). The mixture was shaken at RT for 30 min, and then heated to 60–70 overnight (16 h). The resin was filtered and washed as before and dried. The produce N-aminoquinazolinones were cleaved from the resin by TFA/CH2Cl2 (1:1, v/v).

Example 8

Procedures for the Preparation of a 5760-member Library of 3-Hydroxyaginazolinone Step-1: Reaction of N-hydroxylamine on solid support with 15 isatoic anhydrides: N-hydroxylamine on Wang resin (1.0 mmol/g loading, 4.0 g, 4.0 mmol) and 15 different isatoic anhydride (5.0 eq, 20 mmol) and DAMP (1.2 mmol) in 20 mL DMF were shken in glass vials at 60 C. for 40 h. The mixture were filtered and washed thoroughly with warm DMF (2×15 mL), CH3OH (2×15 mL) and CH2Cl2 (2×15 mL) and dried. A small sample was tkane from each vial and cleaved by FRA/CH2Cl2 and checked by HPLC which conformed the complete reaction of N-hydroxylamine with the anhydride.

The 15 N-hydroxybenzamides on solid support were then dividend into five groups by mixing three benzamides per group.

Step-2: Reaction of benzamides with 16 Fmoc-amino acids: The 15 N-hydroxybenzamides on solid support were then divided into five groups by mixing three benzamides per group by suspending and stirring the resin in CH2Cl2 followed by drying (weight of resin per group: ca. 12–13 g, 12 mmol). Each group of resin was then evenly distributed into 16 glass vials (ea. 0.8 per vial, 0.75 mmol) (total vials –5×16=80). A solution of DMAP (5 mL, 7.0 eq., 5.25 mmol) in dimethylacetamide (DMAC) (note: reaction in DMAC is clearer than that in DMF for this step) was added to each vial, followed by a solution of each of the 16 Fmoc-amino acids in DMAC (5 mL, 6.0 eq. 4.5 mmol). The vials (total 5 groups of resinx16 of Fmoc-amino acids=80 vials) were shaken to mix the resin and the reagents at rt. A solution of PyBrOP in DMAC (4 mL, 5 eq., 3.75 mmol) was than added to each vial. The vials were shaken at rt for 30–45 min, then at 60–65° C. overnight (17–22 h). Samples were taken and cleaved to check by HPLC to confirm the completion of the reaction. The resins were then collected by filtration and washed thoroughly with DMF, Ch3OH, and CH2Cl2 (2×10 mL each) and dried to give the Fmoc-protected quinazolinones on resins.

Step-3a: Removal of Fmoc-protecting group: Each of the 80 groups of resins from Step-2 was suspended in 10 mL 30(by volume) of piperdine in DMF and shaken at rt for 2 h. The resins were then filtered and washed with DMF, $CH_3OH$ and $CH_2Cl_2$ (each solvent was used 2× (or 3×, respectively) (each 2×10 mL) and dried to give the free amino quinazolinones on resins.

Step-3b: Reaction with 8× chloroformates, 8× sulfonyl chlorides and 8× isocyanates: Each of the 80 groups of resins from Step-3a were then evenly distributed into 24 wells of a reactor block as a suspension of CH2Cl2CH3OH (total wells used=80×24=1920). The solvents were than removed and the resins (ca 0.03 mmol per well) were suspended in a solution of DMF (0.3 mL) in the presence of diisopropyl-ethylamine (DIPEA) (10 eq., 0.3 mmol). Each of eight chloroformates, eight sulfonyl chlorides and eight isocyanates (5.8 eq each, 0.13 mmol) in 0.3 ml of DMF was then added individually to the 24 wells. The reactor was shaken at rt overnight. The resins were then filtered and washed with DMF, $CH_3OH$, and $CH_2Cl_2$ (each 3×3 mL) and dried to give finally 1920 wells of quinazolinones (3 compounds per well) on resins.

Step-4: Cleavage from Resins to give N-hydroxyquinaxolinones: The 1920 wells of resins from Step 3b were treated with 1:1 TFA/CH2Cl2 (1 mL) at rt for 1–2 h with shaking. The resins were then filtered and washed with 0.5 mL of 1:1 TFA/CH2Cl2. The combined solutions were collected in a 96-well titre plate and dried under vacuum to remove the excess TFA/CH2Cl2. The resulting products were analyzed by HPLC and MS to confirm the purity and structure of the products. The final products (total number is 5760 as 3 compounds per well) were stored in a freezer for future biological screenings.

The present invention is versatile and can be used to prepare libraries of N-amino- and N-hydroxy-quinazolinones having biological activity, including, but not limited to, hypotensive, antibacterial, antifungal, antipyretic and CNS depressant activity.

The present invention is not to be limited in scope by the specific embodiments disclosed in the examples, which are intended as illustrations of a few aspects of the invention, and any embodiments which are functionally equivalent are considered to be within the scope of this invention. Indeed, various modifications of the invention in addition to those shown and described herein will become apparent to those skilled in the art and are intended to fall within the claimed subject matter. As the cited patents or publications may provide further useful information, the cited references are hereby incorporated by reference in their entireties.

What is claimed is:

1. A method for synthesizing a 3-hydroxy quinazolinone, comprising:
    (a) reacting a free amine moiety bound to a solid support with an appropriate isatoic anhydride to afford a 2-aminobenzamide bound to said solid support;
    (b) reacting said 2-aminobenzamide with a carboxylic acid in the presence of an activating agent to afford a 3-hydroxy quinazolinone bound to said solid support; and
    (c) reacting said 3-hydroxy quinazolinone bound to said solid support under acidic hydrolysis conditions to yield unbound 3-hydroxy quinazolinone.

2. The method of claim 1, wherein said acidic hydrolysis conditions comprise trifluoroacetic acid ranging from about 20% v/v to about 95% v/v in methylene chloride.

3. A method of synthesizing an N-hydroxy quinazolinone on a solid support which comprises:
    (a) selecting a solid support comprising at least one compound covalently attached to said solid support which compound comprises a moiety having at least one nucleophilic site;
    (b) reacting said moiety of said compound covalently attached to said solid support with a diverse array of isatoic anhydrides in an aprotic organic solvent at an appropriate temperature range to afford a 3-alkoxy-2-aminobenzamide;
    (c) reacting said 3-alkoxy-2-aminobenzamide bound to said solid support with a carboxylic acid in the presence of an activating agent or an acid chloride and a coupling agent to afford a 3-alkoxy quinazolinone bound to said solid support.

4. The method according to claim 3 wherein said compound covalently attached to said solid support is hydroxylamine.

5. The method according to claim 3 where said nucleophilic site is an amine moiety.

6. The method according to claim 3 wherein said coupling agent is bromo-tris-pyrrolidino-phosphonium hexafluorophosphate.

7. The method according to claim 3 wherein said aprotic organic solvent is dimethylformamide.

8. The method according to claim 3 where said appropriate temperature range is between about 80° C. to about 90° C.

9. A method for synthesizing a 3-amino quinazolinone, comprising:
    (a) reacting a hydrazine moiety with a free amino group bound to a solid support with an appropriate isatoic anhydride to afford a 1,2 disubstituted anthraniloylhydrazine;
    (b) reacting said 1,2 disubstituted anthraniloylhydrazine with a carboxylic acid in the presence of an activating agent to afford a 3-amino quinazolinone bound to said solid support, and
    (c) reacting said 3-amino quinazolinone bound to said solid support under acidic hydrolysis conditions to yield unbound 3-hydroxy quinazolinone.

10. The method of claim 9, wherein said acidic hydrolysis conditions comprise trifluoroacetic acid ranging from about 20% v/v to about 95% v/v in methylene chloride.

11. A method of synthesizing an N-amino quinazolinone on a solid support which comprises:
    (a) selecting a solid support comprising at least one compound covalently attached to said solid support which compound comprises a moiety having at least one nucleophilic site;
    (b) reacting said moiety of said compound covalently attached to said solid support with a diverse array of isatoic anhydrides in an aprotic solvent to afford a 1,2 disubstituted anthraniloyl hydrazine; and
    (c) reacting said 1,2 disubstituted anthraniloyl hyrdrazine bound to said solid support with a carboxylic acid in the presence of a coupling agent to afford a 3-hydrazino-quinazolinone bound to said solid support.

12. The method according to claim 11 wherein said compound covalently attached to said solid support is a carbazate.

13. The method according to claim 11 wherein said nucleophilic site is a hydrazine moiety with a free amino group.

14. The method according to claim 11 wherein said coupling agent is bromo-tris-pyrrolidino-phosphonium hexafluoro phosphate.

* * * * *